United States Patent [19]

Höhn et al.

[11] Patent Number: 5,756,847
[45] Date of Patent: May 26, 1998

[54] BIS(DIORGANOPHOSPHINO)METHANES

[75] Inventors: Arthur Höhn, Kirchheim; Justin Wolf, Weikersheim, both of Germany

[73] Assignee: BASF Aktiengesellschaft, Ludwigshafen, Germany

[21] Appl. No.: 874,533

[22] Filed: Jun. 13, 1997

Related U.S. Application Data

[62] Division of Ser. No. 756,478, Nov. 26, 1996, Pat. No. 5,698,743.

[30] Foreign Application Priority Data

Nov. 29, 1995 [DE] Germany ............... 195 44 448.5

[51] Int. Cl.⁶ ............................................. C07F 9/50
[52] U.S. Cl. ............................................. 568/8
[58] Field of Search ................................. 568/8

[56] References Cited

PUBLICATIONS

CA:80:83138 abstract of "Synthesis of menthyl and neo-menthyldiphenylphosphine" Morrison, J Org Chem 39(2) pp. 270–272, 1974.

CA:123:112179 abstract of "Regio and stereoselectivity in the hydrogenation of aryl phosphines by niobium aryloxide compounds", Potyen, J Chem Soc Chem Comm (8) pp. 849–851, 1995.

CA:117:90380 abstract of "Catalytic hydrogenation of arylphosphines by niobium aryloxid compounds" Yu, J Chem Soc Chem Comm (8) pp. 632–633, 1992.

*Primary Examiner*—Gary Geist
*Assistant Examiner*—Jean F. Vollano
*Attorney, Agent, or Firm*—Keil & Weinkauf

[57] ABSTRACT

Preparation of methylene-bridged compounds of the formula I

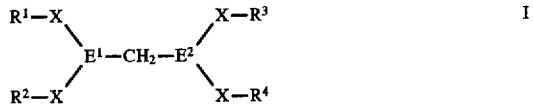

where $R^1$ to $R^4$ are identical or different and are each saturated $C_1$–$C_{30}$-hydrocarbyl, unsubstituted phenyl, phenyl substituted by substituents inert under the reaction conditions, or hydrogen. $E^1$ and $E^2$ are identical or different and are each phosphorus, arsenic or antimony, and X is a chemical bond or oxygen by reacting a tin compound of the general formula II $$R_3^5Sn\text{—}CH_2M,\qquad II$$

where $R^5$ is $C_1$–$C_{20}$-hydrocarbyl and M is an alkali metal, with a compound of the general formula III

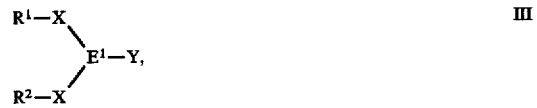

where Y is halogen, metallating the thus-obtained tin compound of the general formula IV

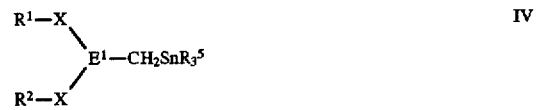

with an alkali organometallic, and reacting the product with a compound of the general formula V

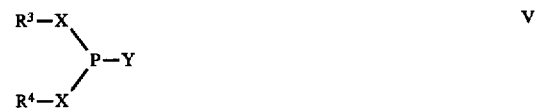

to give a methylene-bridged compound of the formula I. And novel 45 bis(diorganophosphino)methanes.

4 Claims, No Drawings

5,756,847

BIS(DIORGANOPHOSPHINO)METHANES

This is a divisional of application Ser. No. 08/756,478, filed Nov. 26, 1996 now U.S. Pat. No. 5,698,743.

BACKGROUND OF THE INVENTION

1. Field of the Invention

Preparation of methylene-bridged hetero compounds and novel bis(diorganophosphino)methanes This invention relates to novel bis(diorganophosphino) methanes.

Bis(dialkylphosphino)alkanes and bis(diarylphosphino) alkanes represent an important group of ligands in organometallic chemistry and are of interest especially for organometallic catalysts. For instance, bis(diorganophosphino) methanes and metal compounds can be reacted to prepare four-membered ring chelates having small phosphorus-metal-phosphorus angles. Such compounds, especially those containing the metals cobalt, rhodium, iridium, nickel, palladium and platinum in the oxidation states of 0 to 3, are compounds sought after for use as catalysts and as intermediates of catalytic cycles. The compounds sought after serve as ligands for transition metals for homogeneous catalysts in hydrogenations, hydroformylations, carbonylations and in the oligomerization and cooligomerization of unsaturated compounds.

However, bis(diphosphino)methanes tend to form two- or multicenter complexes instead of the four-membered, metal-containing rings desired. Therefore, the stabilization of mononuclear four-membered ring chelate complexes requires tailor-made bis(diphosphino)methanes having specific steric and electronic properties in order that polynuclear structures may be destabilized.

2. Description of Related Art

Wide industrial use of bis(diorganophosphino)methanes was up to now prevented by the difficult accessibility of these compounds. Thus, Karsch (Z. Naturforsch. 38b (1983) 1027) describes the synthesis of bis(di-tert.-butylphosphino) methane in unsatisfactory yields from bis (dichlorophosphino)methane and tert.-butyllithium.

DE-A 41 34 772 teaches that better yields are obtained when di-tert.-butyl-chlorophosphane is reacted with a metallated di-tert.-butylphosphinomethane. A problem, however, is the formation of tetraorganobisphosphanes, which is observed especially with other sterically demanding ligands on the phosphorus, since these compounds are difficult to separate from the desired products.

It is an object of the present invention to make available a process allowing the preparation of bis (diorganophosphino)methanes in good yields. Also to be prepared are bis(diorganophosphino)methanes having sterically demanding ligands, ligands having optically active centers being especially sought after because of the special catalytic properties associated with this property. Finally, novel bis(diorganophosphino)methanes are to be made available.

SUMMARY OF THE INVENTION

We have found that this object is achieved by a process for the preparation of methylene-bridged compounds of the formula I

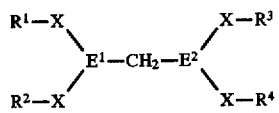

where $R^1$ to $R^4$ are identical or different and are each saturated $C_1$–$C_{30}$-hydrocarbyl, unsubstituted phenyl, phenyl substituted by substituents inert under the reaction conditions, or hydrogen, $E^1$ and $E^2$ are identical or different and are each phosphorus, arsenic or antimony, and X is a chemical bond or oxygen, which comprises reacting a tin compound of the formula II $$R_3^5Sn\text{---}CH_2M, \quad \text{II}$$

where $R^5$ is $C_1$–$C_{20}$-hydrocarbyl and M is an alkali metal, with a compound of the formula III

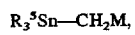

where Y is halogen, metallating the thus-obtained tin compound of the formula IV

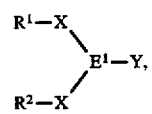

with an alkali organometallic, and reacting the product with a compound of the formula V

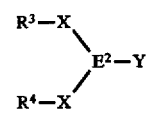

to give a methylene-bridged compound of the formula I.

This invention also provides novel bis (diorganophosphino)methanes.

The process according to the invention makes possible the preparation of compounds of the formula I. The substituents have the following meanings:

$R^1$–$R^4$: saturated $C_1$–$C_{30}$-hydrocarbon radicals, preferably $C_4$–$C_{14}$ radicals such as tert.-butyl, tert.-amyl and 2-ethylhexyl; especially preferred are radicals carrying a tertiary carbon in a position beta to the heteroatom $E^1$ or $E^2$, such as menthyl, longifolyl, alpha-pinyl, betapinyl, 3-caryl and 2-caryl; also suitable are phenyl radicals, which may carry one to five substituents inert under the reaction conditions;

$E^1$, $E^2$: phosphorus, arsenic, antimony, preferably phosphorus; the radicals are preferably identical;

X: a chemical bond or oxygen, preferably a chemcial bond.

The compounds of the formula I are obtainable by a multi-step process. As starting material there may be used a metallated tin compound of the formula II, where the radicals have the abovementioned meanings. $R^5$ is preferably phenyl or methyl, M is preferably lithium or sodium. The compounds of the formula II are obtainable in a conventional manner by reacting the appropriate halostannanes, especially the iodostannanes, with alkali organometallics such as butyllithium or methyllithium. The compounds of the formula II are reacted with a heteroatom compound of the formula III. These compounds carry a halogen such as fluorine, chlorine, bromine or iodine, preferably chlorine. They are obtainable in a manner known per se, for example by reacting halogen compounds of phosphorus, arsenic or antimony with metallated hydrocarbons with elimination of metal halide. The compounds of the formulae II and III are preferably reacted in stoichiometric amounts. In a preferred embodiment, the reaction is carried out in an inert solvent such as toluene, hexane or mixtures thereof. The starting materials are reacted in the cold, for example at from −70° to −20° C. After the reaction has ended, the corresponding compound of the formula IV can be isolated by known methods, for example extraction of the alkali metal halide formed with water, drying of the organic phase and crystallization, if necessary after a change of solvent.

The compound thus obtained of the formula IV is reacted with an alkali organometallic. Phenyllithium is preferred, but compounds such as butyllithium and methyllithium are also suitable. Stoichiometric amounts of the alkali organometallic are preferred. Excesses may be used, but they have to be destroyed prior to any further reaction. Especially preferred is the elimination of tetraphenyltin from compound IV, because the former crystallizes easily and can thus be easily removed from the reaction mixture. To the reaction mixture is then added a compound of the formula V, which is obtainable analogously to compounds of the formula III. For this reaction as well, a stoichiometric reaction of the starting materials is preferred. In a preferred embodiment, the compound of the formula V is added to the reaction mixture at temperatures of from −70° to −20° C. After extraction with water, the product is isolated by crystallization from the organic phase.

Specific compounds I are preferably bis(dimenthylphosphino)methane, furthermore bis(di-tert.-butylphosphino)methane, (dimenthylphosphino)(diphenylphosphino)methane, (dimenthylphosphino)(di-tert.-butylphosphino)methane and (di-tert.-butylphosphino)(diphenylphosphino)methane and compounds where $R^1$ and $R^2$ are each menthyl and $R^3$ and $R^4$ are each phenyl or $C_4$–$C_{14}$-hydrocarbon radicals, having in a position beta to $E^2$ a tertiary carbon.

The process according to the invention makes possible the preparation of much sought-after methylene-bridged heteroatom compounds of group 15 of the Periodic Table in high yields.

EXAMPLES a) Preparation of $(men)_2P$—$CH_2$—$SnPh_3$ (men=menthyl) Menthyl is the radical

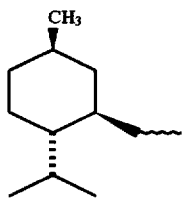

$(men)_2PCl + LiCH_2$—$SnPh_3$ ⟶ $(men)_2P$—$CH_2$—$SnPh_3$ + LiCl

To a solution of 21.27 g (43.32 mmol) of $ICH_2$—$SnPh_3$ in 200 ml of toluene was added dropwise at −55° C. within 30 min 16.05 ml of a 2.7M solution of butyllithium (43.32 mmol) in hexane. The mixture was stirred for 30 min, at which point, again at −55° C., a solution of 14.94 g (43.32 mmol) of $(men)_2PCl$ in 60 ml of toluene were slowly added. The reaction solution was then carefully warmed, stirred for 2 h at −15° C. and for 1 h at room temperature, and cooled to 0° C., at which point 50 ml of $H_2O$ were added. The phases were then separated, the organic phase was washed two times with 50 ml $H_2O$ each time and dried by stirring for 5 min over $Na_2SO_4$. After filtration, the solvent was distilled off under reduced pressure, the residue was extracted with 200 ml of warm pentane, and the solution was concentrated by boiling until crystallization set in, and then slowly cooled to −18° C. A colorless, fluffy precipitate sensitive to hydrolysis was formed, which was filtered off and dried under reduced pressure. Concentrating the mother liquor to about 30 ml and cooling to −18° C. afforded more product.

Yield: 20.16 g (69%); Melting point: 120°–121° C.;

$^{13}$C-NMR ($C_6D_6$): δ139.54 (d,J(PC)=1.8 J($^{117/119}$ SnC)= 485.6 Hz, ipso-C of $C_6H_5$), 137.59 (d,J(PC)=1.3 J($^{117/119}$ SnC)=35.9 Hz, ortho-C of $C_6H_5$), 129.20 (s,para-C of $C_6H_5$), 128.79 (s,J($^{117/119}$ SnC)=50.1 Hz, meta-C of $C_6H_5$), 45.82 (d,J(PC)=19.2 Hz, CH of men), 44.76 (d,J(PC)=9.4 Hz, CH of men), 40.20 (d,J(PC)=19.1 Hz, CH of men), 39.11 (s, $CH_2$ of men), 36.28 (s, $CH_2$ of men), 35.33 (s, $CH_3$ of men), 35.22 (s, $CH_2$ of men, 33.91 (s,CH of men), 33.69 (d,J(PC)=23.8 Hz, CH of men), 33.66 (s, CH of men), 28.07 (s, CH of men), 27.60 (d,J(PC) 6.4 Hz, CH of men), 26.13 (d,J(PC)=8.4 Hz, $CH_2$ of men), 25.52 (d,J(PC)=6.3 Hz, $CH_2$ of men), 23.22, 22.98, 22.19, 21.97, 16.10, 15.67, (all s, $CH_3$), 0.46 (d,J(PC)=45.6 Hz, P—$CH_2$).

$^{31}$P-NMR ($C_6D_6$): δ-31.87 (s,J($^{117/119}$ SnP)=115.5 Hz)

b) Preparation of $(men)_2P$—$CH_2$—$P(men)_2$

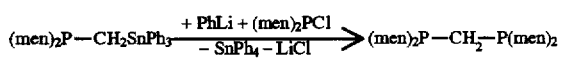

To a solution of 13.20 g (19.60 mmol) of $(men)_2P$—$CH_2$—$SnPh_3$ in 200 ml of $Et_2O$ was added at 20° C. within 30 min 11.04 ml of a 1.73M solution of phenyllithium (19.10 mmol) in diethyl ether/cyclohexane (30:70), and the mixture was stirred for 45 min. After only a few minutes, $SnPh_4$ began to precipitate as a colorless solid. The reaction mixture was then cooled to −25° C., and a solution of 6.59 g (19.10 mmol) of $(men)_2PCl$ in 100 ml of $Et_2O$ was added dropwise within 45 min. Stirring was continued for a further 60 min at −25° C., the cooling bath was removed and the solvent was distilled off under reduced pressure as soon as the mixture had reached room temperature. The residue was extracted with 250 ml of pentane, and 50 ml of $H_2O$ were added to the extract. The phases were then separated, and the organic phase washed two times with 50 ml of $H_2O$ each time and dried over $Na_2SO_4$. After filtration, the solvent was distilled off under reduced pressure and the residue was recrystallized from 170 ml of propanol. A colorless, air-sensitive solid was obtained.

Yield: 7.84 g (65%); Melting point 161°–163° C.;

$^{13}$C-NMR ($C_6D_6$): δ46.79 (vt,N=20.5 Hz,CH), 44.84 (vt, N=11.2 Hz,CH), 40.45 (s, $CH_2$ of men), 40.11 (vt,N=9.8 Hz,CH), 36.82 (s, $CH_2$ of men), 35.43 (s, $CH_2$ of men), 35.34 (s,$CH_2$ of men), 34.24 (s, 2x CH), 33.07 (vt,N=22.7 Hz,CH), 28.00 (vt,N=22.3 Hz,CH), 27.70 (vt,N=26,1 Hz,CH), 26.28 (vt,N=7.9 Hz,$CH_2$ of men), 25.56 (vt,N=6.1 Hz,$CH_2$ of men), 23.19, 23.00, 22.39, 21.78, 15.72, 15.56 (all s, $CH_3$), 11.80 (t,J(PC)=28.5 Hz), P—$CH_2$—P). v is a virtual spin system.

$^{31}$P-NMR ($C_6D_6$): δ36.73 (s).

We claim:
1. A bis(diorganophosphino)methane selected from the group consisting of bis(dimenthylphosphino)methane, (dimenthylphosphino)(diphenylphosphino)methane and (dimenthylphosphino)(di-tert.-butylphosphino)methane.
2. Bid(dimenthylphosphino)methane.
3. (Dimenthylphosphino)(diphenylphosphino)methane.
4. (Dimenthylphosphino)(di-tert.-butylphosphino)methane.

* * * * *